US011419705B2

(12) United States Patent
Cueille et al.

(10) Patent No.: US 11,419,705 B2
(45) Date of Patent: Aug. 23, 2022

(54) PROCESS FOR THE PREPARATION OF NANOSTRUCTURES ON A DENTAL IMPLANT

(71) Applicant: STRAUMANN HOLDING AG, Basel (CH)

(72) Inventors: Christophe Cueille, Basel (CH); Simon Berner, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 130 days.

(21) Appl. No.: 16/651,905

(22) PCT Filed: Sep. 27, 2018

(86) PCT No.: PCT/EP2018/076309
§ 371 (c)(1),
(2) Date: Mar. 27, 2020

(87) PCT Pub. No.: WO2019/063711
PCT Pub. Date: Apr. 4, 2019

(65) Prior Publication Data
US 2020/0261188 A1 Aug. 20, 2020

(30) Foreign Application Priority Data
Sep. 27, 2017 (EP) ..................................... 17193452

(51) Int. Cl.
*A61C 8/00* (2006.01)
(52) U.S. Cl.
CPC .......... *A61C 8/0015* (2013.01); *A61C 8/0037* (2013.01); *A61C 8/0087* (2013.01); *A61C 2008/0046* (2013.01)
(58) Field of Classification Search
CPC ................ A61C 8/0037; A61C 8/0087; A61C 2008/0046
See application file for complete search history.

(56) References Cited

U.S. PATENT DOCUMENTS 9,642,680 B2 * 5/2017 Berner .................... C25D 7/00
2007/0068827 A1 * 3/2007 Jemelin ................ A61C 8/0087
206/63.5

(Continued)

FOREIGN PATENT DOCUMENTS

EP 1 523 954 A1 4/2005
EP 2 022 447 A1 2/2009

(Continued)

OTHER PUBLICATIONS

Mar. 31, 2020 International Preliminary Report on Patentability issued in International Patent Application No. PCT/EP2018/076309.

(Continued)

*Primary Examiner* — Ralph A Lewis
(74) *Attorney, Agent, or Firm* — Oliff PLC

(57) ABSTRACT

A process for the preparation of a topography for improved fibrin network formation and cell mineralization on at least a portion of a dental implant made of a binary titanium-zirconium alloy, the portion being destined to be embedded in a patient's jawbone and to be in contact with the jawbone via a bone-contacting surface, the process includes the subsequent steps of a) subjecting the bone-contacting surface of the dental implant to a sandblasting treatment, b) etching the sandblasted bone-contacting surface, and c) treating the sandblasted and etched bone-contacting surface with water or an aqueous solution for a duration of more than two days, during which nanostructures continuously grow on the bone-contacting surface, the nanostructures extending in at least two dimensions to 200 nm at most. The process is characterized in that the treatment of b) is carried out at a temperature from 40° C. to 60° C.

14 Claims, 2 Drawing Sheets

200 nm

(56) References Cited

U.S. PATENT DOCUMENTS

| | | | | |
|---|---|---|---|---|
| 2010/0173264 A1* | 7/2010 | Fredriksson | ............... | C23C 8/10 |
| | | | | 433/173 |
| 2014/0342316 A1* | 11/2014 | Berner | ............... | A61C 13/0007 |
| | | | | 433/174 |
| 2016/0120626 A1* | 5/2016 | Berner | ............... | C25D 7/00 |
| | | | | 433/201.1 |
| 2018/0153660 A1* | 6/2018 | Berner | ............... | A61C 13/0006 |

FOREIGN PATENT DOCUMENTS

| | | |
|---|---|---|
| WO | 2013/056844 A1 | 4/2013 |
| WO | 2014/195025 A2 | 12/2014 |
| WO | 2016/189099 A1 | 12/2016 |

OTHER PUBLICATIONS

Nov. 14, 2018 International Search Report issued in International Patent Application No. PCT/EP2018/076309.

\* cited by examiner 200 nm 200 nm 200 nm

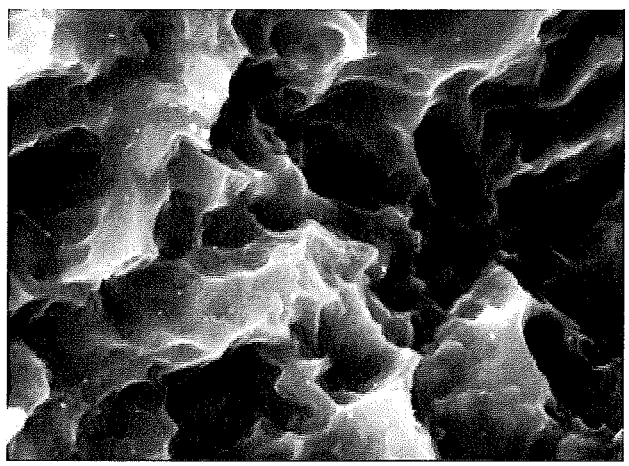
200 nm      Fig. 4
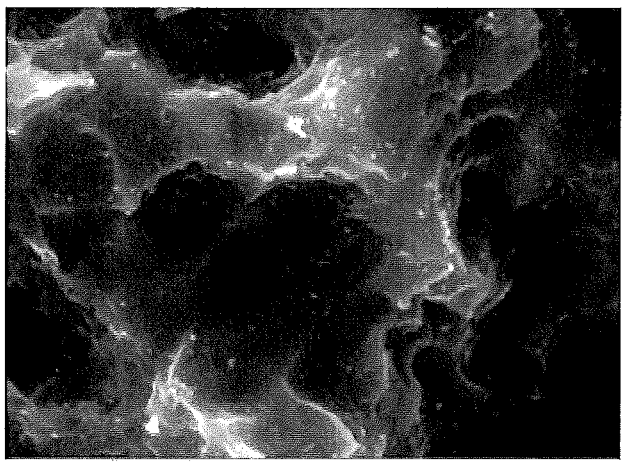
200 nm      Fig. 5
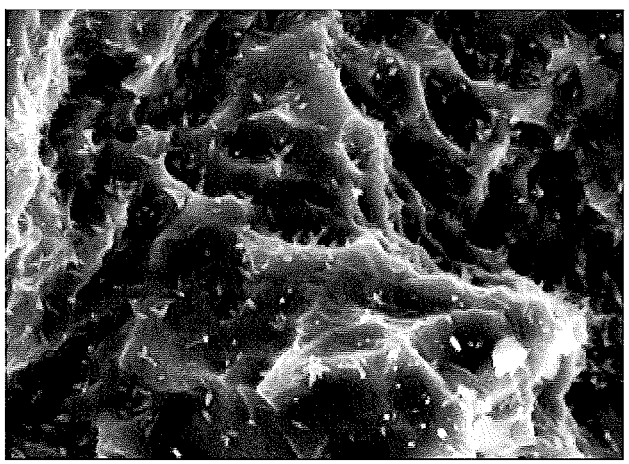
200 nm      Fig. 6

PROCESS FOR THE PREPARATION OF NANOSTRUCTURES ON A DENTAL IMPLANT

The present invention relates to a process for the preparation of a topography for improved fibrin network formation and cell mineralization on at least a portion of a dental implant made of a binary titanium-zirconium alloy, and to a dental implant obtainable by this process.

Dental implants are well known in the art. They generally consist of a material, which is biocompatible and which additionally has favourable mechanical properties.

Currently used dental implants are often made of titanium, which apart from being biocompatible exhibits a high mechanical strength.

Apart from pure titanium, titanium alloys, in particular TiZr, Ti6Al4V (TAV) or Ti6Al7Nb (TAN), have been suggested as material for dental implants, in particular in view of their superior mechanical properties, specifically their low specific weight, their high tensile strength and their high fatigue strength.

An especially well-suited binary titanium-zirconium alloy is described in WO 97/29624, said alloy comprising a zirconium content of less than 25 wt-%, but more than 5 wt-%, and having mechanical properties superior to those of unalloyed and cold-formed titanium.

Besides the good biocompatibility of both pure titanium and of titanium alloys, the acceptance of the human body towards a dental implant made of these materials is to an important degree determined by the dental implant's surface. When detected as a foreign object and rejected by the immune system, the dental implant may cause inflammation, which not only causes pain to the patient but often also leads to the necessity of follow-up surgery to remove or replace the implant.

In order to avoid rejection of the dental implant by the human body, the implant surface must be engineered in a manner that cells attach to it and that natural body tissue, specifically bone tissue or soft tissue, starts growing around it.

In particular, it is required that a direct structural and functional connection between living jawbone and the implant surface is achieved shortly after implantation. This is referred to in the art as "osseointegration", which stands for the implant's tendency to safely ossify within a short healing time so that a permanent bond between implant and bone is obtained.

The interaction between the surface of the implant and the body fluid as well as the surrounding bone tissue is governed by proteins which adhere, i.e. adsorb, to the surface once the implant gets in contact with blood, and in particular by the fibrin network formed on the implant surface. It is assumed that the proteins adsorbed on the implant surface, particularly the fibrin network formed, influence(s) the cellular behaviour, e.g. the differentiation and mineralization, of the bone cells. In order to achieve a fast and strong interaction between the implant and the bone tissue, protein adherence, and in particular fibrin network formation, on the surface is thus of paramount importance.

One important factor that influences protein adherence is the hydrophilicity of the surface.

Recently, it has been found that also the presence of specific nanostructures plays an important role in the adherence of proteins.

In this regard, WO 2013/056844 describes a process for providing structures for improved protein adherence on the surface of a body, specifically an implant. The process comprises the step of storing an acid-etched basic body in an aqueous solution, by which nanostructures are formed on the surface of the basic body.

Also, WO 2014/195025 deals with the formation of nanostructures on a dental implant, but for a different purpose, namely for obtaining a strong interaction between a dental implant and the surrounding soft tissue. In this regard, WO 2014/195025 suggests a surface topography, which is smooth when regarded in macroscopic and microscopic scale, but nevertheless provides a nanoscopic structure due to the presence of nanostructures.

On dental articles made of titanium, the technology according to WO 2013/056844 leads to the formation of nanostructures within weeks.

However, for dental implants made of a binary titanium-zirconium alloy, a relatively long maturation time of 6 months or even longer is needed for the nanostructures in the desired number, size and shape to be formed.

Despite the material's superior mechanical properties, dental implants made of binary titanium-zirconium alloy therefore suffer from requiring a long maturation time for the nanostructures to grow; this ultimately results in more time and effort until the dental implant exhibits its optimum surface topography, which apart from a macroscale and a microscale topography also includes a nanoscale topography.

In consideration of the above, the object of the present invention is thus to provide a simple process for preparing a topography for improved fibrin network formation and cell mineralization on a dental implant made of a binary titanium-zirconium alloy, said process allowing the desired topography to be prepared within a relatively short time. In particular, the process shall allow nanostructures in the desired number, size and shape to be formed within a much shorter time frame than when treating them by known processes. Ultimately, improved osseointegrative properties of the dental implant shall thus be achieved by the process of the present invention.

According to a particular aspect of the invention, the process shall allow to be easily integrated into the workflow of established processes for preparing dental implants, and more particularly shall be applicable to a dental implant that is already packaged and sterilized.

The object is solved by the process according to claim 1. Preferred embodiments are defined in the dependent claims.

According to claim 1, the present invention thus relates to a process for the preparation of a topography for improved fibrin network formation and cell mineralization on at least a portion of a dental implant made of a binary titanium-zirconium alloy, said portion being destined to be embedded in a patient's jawbone and to be in contact with the jawbone via a bone-contacting surface. The process comprises the subsequent steps of a) subjecting the bone-contacting surface of the dental implant to a sandblasting treatment,
b) etching the sandblasted bone-contacting surface, and
c) treating the sandblasted and etched bone-contacting surface with water or an aqueous solution for a duration of more than two days, during which nanostructures continuously grow on the bone-contacting surface, said nanostructures extending in at least two dimensions to 200 nm at most.

Whereas during the sandblasting of step a) a macroscopic topographical formation is formed, the etching of step b) leads to a microscopic topographical formation superimposing the formation obtained in step a).

This surface combining a macroscopic and a microscopic topographical formation is then subjected to step c), during which nanostructures constantly grow (or evolve) forming retention sites for proteins contributing to an improved blood coagulation and/or an improved cell-surface interaction towards cells of the surrounding tissue.

Without wanting to be bound by the theory, the achievement of an improved blood coagulation and/or cell-surface interaction can be explained by the following mechanism:

When the implant is implanted into bone tissue, it is first contacted by water molecules from the surrounding blood. In a next step, ions and proteins will accumulate and adhere on the implant's surface, but without actually penetrating the material. As mentioned above, this "protein adherence" or "protein adsorption" is assumed to be decisive for later cell responses.

Specifically, nanostructures are formed in step c) in a size, shape and number, in which they form "protein retention structures" allowing for a pronounced and specific adherence of proteins mediating blood coagulation and/or cell attachment. Thus, a fast blood coagulation and, hence, formation and stabilization of the fibrin network can be achieved, which contributes at least partially to a fast and strong attachment of the cells of the surrounding tissue, to an improved cell mineralization and, ultimately, an improved osseointegration of the implant.

This will be further shown by the attached working examples below, according to which the topography allows for an improved adherence of fibrinogen and fibronectin, i.e. proteins to which an important role in the blood coagulation and, hence, the formation of the fibrin network is attributed.

Due to providing a nanoscale topography formed by nanostructures in combination with a macroscale and a microscale topography, the present invention, thus, allows an improved cell-surface interaction to be achieved, which ultimately leads to an improved osseointegration of the implant.

According to the invention, nanostructures (and a nanoscale topography) can now be formed on a binary zirconium-titanium alloy within a much shorter time frame than when applying previously known treatments.

The term "binary zirconium-titanium alloy" as used in the context of the present invention refers to an alloy which is essentially made of zirconium and titanium and which—apart from trace amount of additional alloy components, such as iron, and/or unwanted impurities does not contain further elements. In particular, the term "binary zirconium-titanium alloy" does not encompass tertiary or higher-order zirconium-containing Ti-alloys, such as alloys containing Nb, Ta, Pd and In in addition to TiZr.

The term "nanostructure" (synonymous with the term "ultrafine structure") relates to a structure in the nanoscopic range, i.e. extending in all three dimensions to less than 1 μm, and within the particular meaning of the present invention relates to structures extending in at least two dimensions to 200 nm at most, as mentioned above. More particularly, the "nanostructures" according to the present invention are in general in particulate form and, thus, distinct from nanoscopic cavities or hollows (as achieved by a "nanopitting").

As mentioned, the process of the present invention comprises the step of treating the surface with water or an aqueous solution for a duration of more than two days in order to allow nanostructures to grow in the desired number, size and shape.

Surprisingly, it has been found that by carrying out the treatment of b) in a temperature range from 40° C. to 60° C., preferably from 50° C. to 60° C., nanostructures of the desired number, size and shape can be achieved on a binary titanium-zirconium alloy surface within less than one month, in particular within about 2 weeks.

Thus, by setting the temperature within the range according to the present invention, an improved nanostructure formation is obtained compared to a treatment at a temperature falling outside the mentioned range: For a temperature lower than 40° C., a sufficient number of nanostructures is on the one hand only formed after a very long maturation duration, as mentioned above and as will be shown in the context of the specific working examples. On the other hand, treatment at too high temperatures has been found to lead to an uncontrolled growing of particles, which in size and shape deviate from the ones to be achieved according to the present invention for improving protein adherence and ultimately cell-surface interaction to cells of the surrounding bone tissue.

Although according to the present invention, the bone-contacting surface is subjected to steps a), b) and c), it is understood that the treatment is not necessarily restricted to this particular surface portion of the implant. Thus, embodiments in which additional portions of the implant, and specifically the whole surface of the implant, are subjected to at least one of the mentioned steps are explicitly encompassed by the present invention. This relates in particular to step c), which according to a particularly preferred embodiment is applied to the whole surface of the implant (including the bone-contacting surface).

According to a preferred embodiment, the dental implant is prior to step c) packed in a dental implant packaging, preferably the final dental implant packaging, in which the dental implant is immersed in water or the aqueous solution. In other words, the process of the present invention preferably comprises between step b) and step c) the intermediate step of packing the dental implant in a dental article packaging, in particular the final dental article packaging, and immersing the dental implant in water or the aqueous solution.

According to a particularly preferred embodiment, the process of the present invention, thus, comprises the further step that after the treatment of c) the dental implant is stored in the dental implant packaging being sealed until use, whereby during storing the dental implant is kept immersed in water or the aqueous solution used for the treatment of c).

In this embodiment, water or the aqueous solution has a dual function, firstly as a liquid for the nanostructures formation treatment and secondly as a storage liquid ensuring that the dental article keeps its hydrophilicity. There is, therefore, no need to transfer the dental implant from a first liquid (used for the nanostructure formation) to a packaging containing a second (storing) liquid prior to the sealing of the packaging. Rather, the dental implant is already contained in its final, sealed packaging when carrying out the treatment of c). This allows the process to be very easily integrated into current workflows. In particular, no additional measures for maintaining the dental implant's sterility is required, as would be the case, if the above-mentioned transfer of the dental implant (from one liquid to another) was involved prior to the sealing of the packaging.

With regard to the dental implant packaging, it is preferably made of a material selected from the group consisting of cyclic olefin copolymer (COC), polyethylene (PE), polypropylene (PP), polyether ether ketone (PEEK), polyether ketone ketone (PEKK) and Teflon®. Since all of these materials have been shown to be thermoresistant up to a temperature of beyond 60° C., no negative impact on the package arises from the treatment according to the present invention.

According to a particularly preferred embodiment, the packaging comprises at least two packaging components of different polymeric materials, in particular selected from the group consisting of cyclic olefin copolymer (COC), polyethylene (PE), polypropylene (PP), polyether ether ketone (PEEK), polyether ketone ketone (PEKK) and Teflon®. For any packaging component, the most suitable material for meeting its respective requirements can thus be used. For example, a first material can be used for a tube, in which the dental article is to be placed, whereas a second material different from the first material is used for a lid for closing the tube. It has surprisingly been found that even if such a relative complex packaging comprising packaging components of different materials is used, no damage occurs when subjecting the final packaging to the process of the present invention.

In the interest of the nanostructures growing relatively fast and at the same time of a high process safety, a temperature of about 55° C. has been found to be most preferred for the treatment according to step b).

As mentioned above, the process of the present invention can, thus, be integrated into the workflow of established processes for preparing packaged dental articles. For example, it can be applied as a post-treatment to the process for preparing SLActive® dental implants without requiring any changes in the preparation process itself.

As also mentioned above, the present invention allows nanostructures of the desired number, size and shape on a titanium-zirconium alloy to be obtained within a relatively short time frame of less than one month. According to a specific embodiment of the present invention, the treatment of b) is, thus, carried for a duration of 4 weeks at most, preferably 3 weeks at most. Given that the growing of nanostructures generally takes several days at least, the preferred range of the duration of treatment is from 5 days to 4 weeks, preferably from 10 days to 3 weeks, and most preferably from 2 to 3 weeks, since this duration has been found to be sufficiently long for the desired nanostructures to be formed, as mentioned above. Most preferably, the treatment of b) is carried out for a duration of about 2 weeks.

In teaching a treatment duration of more than two days, specifically of more than one week, the approach of the present invention is different from the approach taken in WO 2016/189099, which suggests a treatment with an aqueous solution comprising an oxidative agent, and in this regard teaches a treatment time in the range of hours, most preferably from 0.5 to 2.5 hours.

Specifically, the pH value of the nanostructure growing solution ranges from 2 to 10, preferably from 2 to 9, more preferably from 3 to 7, and most preferably from 4 to 6.

According to a particularly preferred embodiment, the nanostructure growing solution is a physiologic salt solution having a pH value of about 7.4.

Apart from using a physiologic salt solution, good results in view of nanostructure formation have been observed if an acidic solution is used comprising at least one component selected from the group consisting of hydrogen fluoride, nitric acid, hydrochloric acid, sulphuric acid and or mixtures thereof.

In teaching a treatment using a neutral or acidic solution or a solution of low alkalinity, this embodiment is in even clearer distinction from the technology according to WO 2016/189099 teaching a treatment with an aqueous solution comprising an oxidative agent, namely NaOH at a concentration of 0.1 M or more (resulting in a solution of a pH value of 13 or higher).

In comparison to the treatment according to WO 2016/189099 requiring an oxidative agent, the mentioned embodiment of the present invention has the advantage that after treatment no change from a nanostructure growing solution to a storage solution is required. Rather, the dental implant can be packaged in its final form, in which it is typically immersed in a storage solution, and be treated without changing the solution or otherwise applying any changes which would require an opening of the packaging.

According to a preferred embodiment, the dental implant is subjected to a sterilization treatment prior to step c). In this regard, the sterilization treatment is typically carried out after packaging. Thus, nanostructure formation under a sterile environment can be achieved, since as mentioned above an opening of the package is not required for the process of the present invention to be carried out.

With regard to the etching according to step b), an acidic or a basic etching solution can be used. Generally, the use of an acidic etching solution, in particular of an etching solution comprising at least one mineral acid, is preferred.

According to a particularly preferred embodiment, the etching solution comprises or essentially consists of a mixture of HCl and $H_2SO_4$. More particularly, a mixture of HCl and $H_2SO_4$ at a temperature higher than 80° C. is used as an etching solution. Alternatively, any other solution of at least one mineral acid can be used, in particular a solution comprising at least one mineral acid selected from the group consisting of HCl, $H_2SO_4$, $H_3PO_4$ and mixtures thereof.

With regard to the sandblasting of step a), by which a topography in the microscopic scale is formed, it is particularly preferred to use corundum as the sandblasting material, more preferably corundum having a particle size from 150-500 µm. Alternatively or additionally to corundum, other sandblasting materials can be used. In particular, the alternative or additional sandblasting material is selected from the group consisting of zirconia beads, iron-based particles, dicalcium phosphate ($CaHPO_4$), silicon carbide (SiC), boron nitride (BN) and titanium dioxide ($TiO_2$). Examples of commercially available sandblasting material suitable for the present invention includes biphasic calcium phosphate from Anthogyr (Sallanches, France) and Stryker Iron from Stryker (Kalamazoo (Mich.), USA).

With regard to the material, the dental implant is preferably made of a binary titanium-zirconium alloy containing from 13 to 17 wt-%, more preferably from 13 to 15 wt-% of zirconium. This material has been shown to exhibit outstanding properties regarding mechanical stability and biofunctionality; a particularly preferred binary titanium-zirconium containing zirconium in the above-mentioned ranges is available under the trade-name Roxolid® (Institut Straumann AG, Switzerland).

More specifically, the preferred binary titanium-zirconium alloy is further defined by an amount of iron being higher than 0.001 wt-%, preferably higher than 0.005 wt-%, more preferably higher than 0.01 wt-%, notwithstanding that iron is only present in trace amounts. In this regard, it is further preferred that the amount of iron contained in the alloy is less than 0.05 wt-%.

According to a preferred embodiment, the nanostructures are at least predominantly in crystalline phase.

Typically, the nanostructures contain titanium oxide, in particular $TiO_2$, specifically $TiO_2$ in anatase and/or rutile phase. In this regard, the term "titanium oxide" can also encompass crystals, which—apart from titanium and oxygen—contain minor amounts of zirconium, i.e. $Ti_{1-x}Zr_xO_2$ crystals. In addition, the nanostructures can further contain $TiH_2$, although in a minor amount.

The nanostructures can have different shapes including a needle-like shape, a leaf-like shape, a flower-like shape, a sphere-like shape or a nodule-like shape.

In the context of the present invention, the term "needle-like shape" encompasses any shape having a length-to-diameter ratio of more than 1 to 1. Thereby, the diameter is to be understood as the expansion of the nanostructure in a direction perpendicular to the longitudinal direction.

Besides the process described above, the present invention further relates to a dental implant obtainable by the process described above.

In analogy to the above, the dental implant of the present invention is made of a binary titanium-zirconium alloy and comprises a portion, which is destined to be embedded in a patient's jawbone and to be in contact with the jawbone via a bone-contacting surface, and is characterized by nanostructures grown on the bone-contacting surface, said nanostructures extending in at least two dimensions to 200 nm at most.

With regard to their function as retention sites for proteins adhering to the surface, in particular proteins mediation blood coagulation and/or cell-surface interaction, a length-to-diameter ratio of the nanostructures of more than 1 to 1, preferably of at least 1.5 to 1, more preferably ranging from 1.5 to 1 to 4 to 1, has been found to be particularly preferred. In the terminology defined above, the nanostructures have, thus, preferably a needle-like shape, which—when conglomerating—can form a flower-like shape.

As will be shown by way of the specific examples, a particularly high protein adsorbing tendency, in particular towards fibrinogen and fibronectin, and a particularly good cell-surface interaction has been observed for a surface which apart from containing nanostructures formed thereon is highly hydrophilic. According to a further preferred embodiment, the bone-contacting surface, thus, has a hydrophilicity defined by a contact angle of less than 45°, more preferably less than 30°, most preferably less than 10°, when contacted with water.

EXAMPLES

1. Effect of the Process According to the Invention on Nanostructure Formation Discs of a titanium-zirconium alloy (Roxolid® of Institut Straumann AG) having a diameter of 5 mm and a thickness of 1 mm were provided with an SLActive® surface, namely by sandblasting the surface using corundum, acid-etching and immediately after acid etching immersing them in physiologic salt solution. The samples were gamma-sterilized and subjected to a temperature treatment at 55°.

After 1 week, 2 weeks and 3 weeks of treatment, samples were analysed using a scanning electron microscope (Zeiss Supra 55) with a field electron emitter (FE-SEM) and an EDX-detector (Oxford Instruments MicroAnalysis System) for the chemical elements. Further analysis was carried out using X-ray photoelectron spectroscopy (XPS).

For comparative reasons, a further set of samples of the same material mentioned above was stored at room temperature and samples were analysed as described above after 2 weeks, 12 weeks and 26 weeks.

In further comparative experiments, samples of the same material mentioned were treated in a 0.9% NaCl solution at pH 2 at a treatment temperature of 124° C. for 2 hours.

The results are shown in the attached Figures of which

FIG. 4 shows an SEM picture of the comparative sample after storing a room temperature for 2 weeks;

FIG. 5 shows an SEM picture of the comparative sample after storing a room temperature for 12 weeks; and FIG. 6 shows an SEM picture of the comparative sample after storing a room temperature for 26 weeks.

In all figures, a scale corresponding to 200 nm is given at the bottom left corner of the respective picture.

Figure 1:
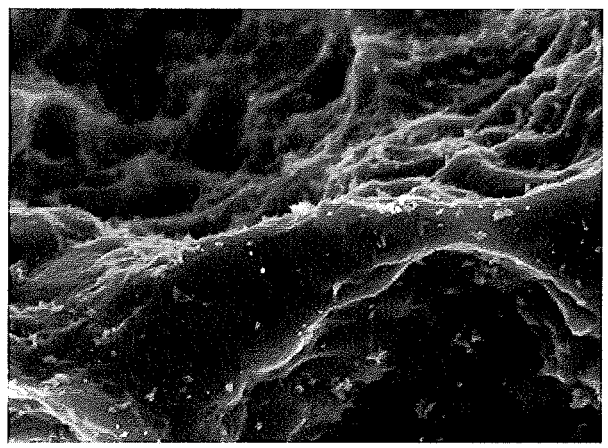
FIG. 1 shows an SEM picture of the sample obtained by the process of the present invention after a treatment of 1 week.
Figure 2:
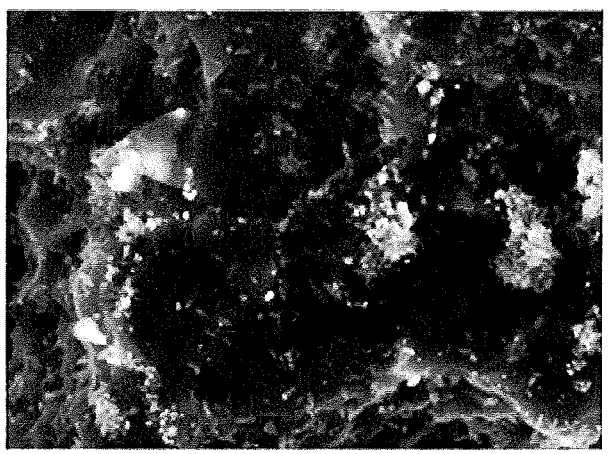
FIG. 2 shows an SEM picture of the sample obtained by the process of the present invention after a treatment of 2 weeks.
Figure 3:
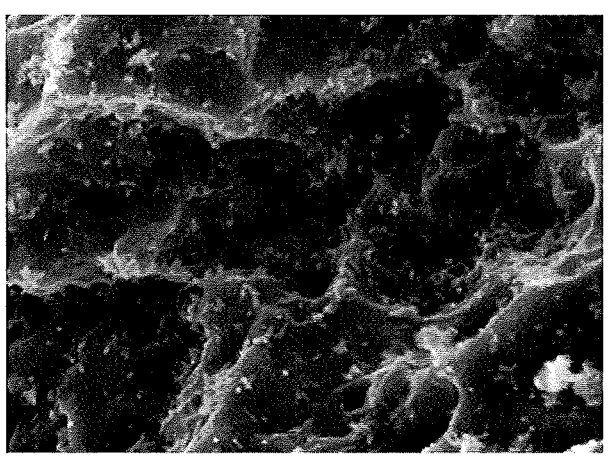
FIG. 3 shows an SEM picture of the sample obtained by the process of the present invention after a treatment of 3 weeks.

As in particular shown in FIG. 2, the desired nanostructures are according to the present invention obtained within a relatively short time frame of only about 2 weeks, whereas for the comparative sample stored at room temperature an acceptable nanostructure formation (i.e. a formation of nanostructures of the desired size, shape and number) has only been observed after 26 weeks.

XPS analysis of the samples according to the present invention revealed a clear increase of the Ti4+ signal (and a decrease of the signal of metallic Ti) in the Ti spectrum, indicating that at least a portion of the nanostructures formed comprise or essentially consist of titanium oxide.

2. Studies on Impact of Surface Treatment on Protein Adsorption, Blood Coagulation and Osteogenic Differentiation of Human Blood Cells (HBC)

2.1. Experimental Procedure

2.1.1. Protein Adsorption

Protein adsorption studies were performed on comparative samples 2.1 as well as on samples 2.2 and 2.3 according to the present invention, the process for obtaining the samples being as follows:

Sample 2.1: Roxolid® discs were sandblasted (corundum) with large grits (particle size 250 to 500 μm), then acid-etched in a boiling mixture of HCl and $H_2SO_4$ followed by cleaning in nitric acid and rinsing in deionized water; finally, the discs were air dried and packed in Al foil.

Sample 2.2: The same sandblasting and etching procedure as for sample 2.1 was applied, followed by placing the sample under nitrogen cover gas to prevent exposure to air, by rinsing in 0.9% NaCl solution and by forming nanostructures in a 0.9% NaCl solution at pH 4 to 6.

Sample 2.3: The same procedure as for sample 2.2 was applied followed by rinsing with ultrapure water using an ultrasonic bath after several months of storage and by drying the rinsed sample in a stream of $N_2$ and packing in Al foil like sample 2.1.

Specifically, protein adsorption studies were performed with protein solutions of bovine fibronectin-HiLyte488 (3 μg $mL^{-1}$) (Lubio Science) and human fibrinogen Alexa Fluor® 488 conjugate (7 μg $mL^{-1}$) (Thermo Fisher Scientific), both dissolved in PBS. For this, surfaces were placed into a 94 well-plate and incubated in 100 μL of protein solution for 15 min at room temperature. Subsequently, surfaces were washed 3× with PBS and analysed with a fluorescence scanner (LS Reloaded™, Tecan Trading AG, Switzerland) using the same settings, i.e. voltage, pinhole, and focal plane, for all samples per condition. Fluorescence intensities (FI) were determined from the images, using the inner 80% surface area of the samples in order to avoid measurement of artefacts at the border of the samples.

2.1.2. In Vitro Studies

For the in vitro studies, human whole blood was obtained from healthy volunteers by standard venipuncture technique. The blood was partially heparinized directly upon withdrawal into a 9 ml S-Monovette tube with 3 IU ml$^{-1}$ sodium heparin (final concentration 0.5 IU heparin/ml blood) and used for the experiments within 1 h after withdrawal.

Samples were placed into a custom-made sample holder made of polytetrafluorethylen (PTFE, Teflon®), which accommodates up to 6 samples. Freshly withdrawn blood (2.8 ml) was added onto the samples. To prevent contact with air the sample holder was closed with a PTFE lid and sealed with parafilm before incubation on a tumbling shaker at 10 rpm at room temperature.

The incubation time was determined for each experiment individually. For this, whole blood was spiked with fluorophore (Alexa 488)-labeled fibrinogen, which allows for live monitoring of the blood coagulation on the samples using fluorescence microscopy. As reference surface, a Roxolid® disc with an SLActive® surface (corresponding to samples 2.2 and 2.3 prior to the nanostructure formation treatment according to the present invention) was used and two time points were chosen representing the beginning of coagulation (t1) and clearly visible layers of fibrin network (t2).

After the period of incubation, blood was removed and the samples were washed 3 times by adding pre-warmed PBS and incubation at 10 rpm for 1 min per washing step. Thereafter, samples were transferred into a 96 well plate.

The samples were analysed using CLSM (confocal laser scanning microscopy) analysis. To this end, the samples were blocked by incubation for 30 min in PBS with 5% goat serum and 1% FCS and platelets were stained with Alexa546-labeled phalloidine for 1 hour at room temperature. The platelets and the fibrin network (visible due to spiking of the blood with Alexa488-labeled fibrinogen) were imaged with a CLSM (10×, 40× magnification). Only one time point (t$_2$) was imaged. On samples showing complete surface-coverage with fibrin, the thickness of the fibrin network was measured from CLSM z-stack images.

In order to analyse the impact of the surfaces on their osseintegration potential, HBCs were cultivated on top of the whole blood pre-incubated surfaces in osteogenic differentiation media. As reference HBCs were cultured on tissue culture plastic either in proliferation or osteogenic differentiation medium. Mineralisation after 28 days of culture was analysed by measuring the Ca$^{2+}$ content in relation to the cell number on the respective surface. For this, HBC proliferation after the period of culture was determined by alamar blue (AB) assay (readout: fluorescence at 530 and 635 nm). AB is reduced by living cells, thereby increasing its own fluorescence. Cell numbers were calculated by interpolating fluorescence readings from a 6-point standard curve (measured from known HBCs numbers after 1 day in culture).

Afterwards, the Ca$^{2+}$ content (Quanti Chrom™ Calcium Assay) on the same samples was assessed. For this, all samples were washed twice with pre-warmed PBS without glucose and lysed (upside down) in 100 µl 1 M HCl for 3 h at 37° C. under constant agitation. Subsequently, 10 µl of each supernatant was transferred to a 96 well-plate and 90 µl of working reagent (equal volumes of solution AB; Quanti Chrom™) containing a phenolsulphonephthalien dye, was added. The dye forms a stable blue coloured complex with free calcium. After 3 min, the absorbance of the solution was measured at 595 nm. Samples were analysed in triplicates. Calcium concentrations were calculated by means of a standard curve.

2.2. Results 2.2.1. Protein Adsorption

Protein adsorption of fibrinogen and fibronectin on top of the surface of samples 2.1, 2.2 and 2.3 was quantitively analysed using fluorophore labelled proteins and a fluorescence scanner. It was found that both protein interact similarly with different structures, the quantitative assessment of protein concentrations showing higher values for sample 2.2 than for sample 2.3 and higher values for sample 2.3 than for sample 2.1.

Thus, both the hydrophilicity as well as the presence of nanostructures obtainable by the process of the present invention play a role in the adsorption of both fibrinogen and fibronectin.

2.2.2. Assessment of Fibrin Network and Fibrin Thickness on Surfaces Incubated with Human Whole Blood Via CLSM The effect of the surfaces on blood coagulation was assessed via CLSM analysing fibrin (fluorophore labelled) and platelets (stained with phalloidin-conjugate).

A qualitative analysis of microscopy images revealed a better coverage for sample 2.2 than for sample 2.3 and a better coverage for sample 2.3 than for comparative sample 2.1

In order to analyse the fibrin coverage in detail, the thickness of the fibrin network was determined in CLSM z-stack images, whereby only surfaces showing a homogenous fibrin network were analysed.

The result of the analysis is given in Table 1, confirming the trend of the qualitative analysis:

TABLE 1

| Sample | Mean fibrin thickness on surface [µm] | Standard deviation [µm] | Number of evaluable experiments |
|---|---|---|---|
| 2.1 | 10.1 | 0.8 | 3 |
| 2.2 | 12.8 | 2.6 | 2 |
| 2.3 | 11.6 | 2.8 | 2 |

2.2.3. Quantification of HBC Mineralization

The effect of different surfaces on HBC mineralization was assessed by measuring the acellular and cellular Ca$^{2+}$ concentration after 28 days of culture in differentiation medium applying the Quanti Chrom™ Calcium Assay kit. Mineralisation was normalized to cell numbers on the respective surfaces obtained from measurements with alamarBlue® cell viability reagent.

Analysing the mineralization of the HBCs after 28 days of culture showed large variations in the observed Ca$^{2+}$ concentrations for the different HBC donors. However, the trend observed between the materials was not affected by the donor variations and was similar in all experiments.

To summarize, a higher trend for HBC mineralization was observed for sample 2.2 compared to sample 2.3, and a higher trend was observed for sample 2.2 compared to comparative sample 2.1. Specifically, if compared to comparative sample 2.1, both the surfaces of samples 2.2 and 2.3 according to the present invention have higher levels of mineralization, the effect being statistically significant.

The invention claimed is:

1. A process for the preparation of a topography for improved fibrin network formation and cell mineralization on at least a portion of a dental implant made of a binary titanium-zirconium alloy, the portion being configured to be embedded in a jawbone of a patient and to be in contact with the jawbone via a bone-contacting surface, the process comprising
  a) subjecting the bone-contacting surface of the dental implant to a sandblasting treatment,
  b) etching the sandblasted bone-contacting surface, and
  c) treating the sandblasted and etched bone-contacting surface with water or an aqueous solution for a duration of more than two days and no more than 4 weeks, during which nanostructures continuously grow on the bone-contacting surface, the nanostructures extending in at least two dimensions to 200 nm at most,
wherein:
  the treatment of step c) is carried out at a temperature in a range from 40° C. to 60° C.,
  prior to step c), the dental implant is packed in a dental implant packaging, in which the dental implant is immersed in the water or the aqueous solution, and
  the packaging is made of a material selected from the group consisting of cyclic olefin copolymer (COC), polyethylene (PE), polypropylene (PP), polyether ether ketone (PEEK), polyether ketone ketone (PEKK), and polytetrafluoroethylene.

2. The process according to claim 1, wherein the treatment of step c) is carried out for a duration of 5 days at least.

3. The process according to claim 1, wherein the treatment of step c) is carried out at a temperature in a range from 50° C. to 60° C.

4. The process according to claim 1, wherein after the treatment of step c), the dental implant is stored in the dental implant packaging that is sealed until use, whereby during the storing, the dental implant is kept immersed in the water or the aqueous solution used for the treatment of step c).

5. The process according to claim 1, wherein the packaging comprises at least two packaging components of different polymeric materials.

6. The process according to claim 1, wherein the aqueous solution has a pH value ranging from 2 to 10.

7. The process according to claim 1, wherein the aqueous solution is a physiologic salt solution.

8. The process according to claim 1, wherein the dental implant is subjected to a sterilization treatment prior to step c).

9. The process according to claim 1, wherein for the etching according to step b), an etching solution comprising a mineral acid is used.

10. The process according to claim 9, wherein the etching solution comprises a mixture of HCl and $H_2SO_4$.

11. The process according to claim 1, wherein the dental implant is made of a binary titanium-zirconium alloy containing from 13 to 17 wt-% of zirconium.

12. A dental implant obtainable by the process according to claim 1, the implant being made of the binary titanium-zirconium alloy and comprising the portion that is configured to be embedded in the jawbone of the patient and to be in contact with the jawbone via the bone-contacting surface on which the nanostructures extending in at least two dimensions to 200 nm at most have been grown.

13. The dental implant according to claim 12, wherein the nanostructures have a length-to-diameter ratio of more than 1 to 1.

14. The dental implant according to claim 12, wherein the bone-contacting surface has a hydrophilicity defined by a contact angle of less than 45° when contacted with water.

* * * * *